United States Patent
Donovan

(10) Patent No.: US 6,447,785 B1
(45) Date of Patent: Sep. 10, 2002

(54) METHOD FOR TREATING HYPERCALCEMIA

(75) Inventor: Stephen Donovan, Capistrano Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 73 days.

(21) Appl. No.: 09/706,174

(22) Filed: Nov. 2, 2000

Related U.S. Application Data

(62) Division of application No. 09/504,538, filed on Feb. 15, 2000.

(51) Int. Cl.$^7$ .................. A61K 39/08; A61K 38/00; A61K 39/02

(52) U.S. Cl. .................. 424/239.1; 424/239.1; 424/236.1; 424/167.1; 514/2; 514/12; 530/350

(58) Field of Search .................. 514/2, 12; 530/350; 424/167.1, 236.1, 239.1

(56) References Cited

U.S. PATENT DOCUMENTS

| | | | |
|---|---|---|---|
| 5,667,808 A | 9/1997 | Johnson et al. | 424/501 |
| 5,674,205 A | 10/1997 | Pasricha et al. | 604/232 |
| 5,980,945 A | 11/1999 | Ruiz | 424/484 |
| 6,007,843 A | 12/1999 | Drizen et al. | 424/488 |
| 6,011,011 A | 1/2000 | Hageman | 514/12 |
| 6,022,554 A | 2/2000 | Lee et al. | 424/423 |
| 6,319,506 B1 * | 11/2001 | Donovan | 424/239.1 |

FOREIGN PATENT DOCUMENTS

WO  WO94/21300  9/1994

OTHER PUBLICATIONS

Ahren, B.; Cholinergic and VIPergic Effects on Thyroid Hormone Secretion in the Mouse; *Peptides*; 1985;6:585–589.

Amenta, F., et al.; Cholinergic Nerves in the Thyroid Gland; *Cell and Tissue Res.* (1978); 195:367–370.

Aoki, K. R.; Preclinical Update on BOTOX® (botulinum Toxin Type A)–Purified Neurotoxin Complex Relative to other Botulinum Neurotoxin Preparations;*Eur. J. Neurol*; 6(Suppl 4):S3–S10; (1999).

Bayliss, et al.; *Thyroid Disease The Facts* 3rd edition; preface; p. 69–70; Oxford University Press (1998).

Boyd, R. S., et al.; The Effect of Botulinum Neurotoxin–B on Insulin Release from a B–Cell Line; *Movement Disorders* (1995); vol. 10, No. 3; Item 19; 376.

Boyd, R. S., et al.; The Insulin Secreting B–Cell Line HIT–15 Contains SNAP–25 Which is a Target for Botulinum Neurotoxin–A; *Movement Disorders* (1995); vol. 10, No. 3; Item 20; 376.

Brandi, M.L., et al.; Interaction of VIPergic and Cholinergic Receptors in Human Thyroid Cell; *Peptides*; 1987; 8:893–897.

Braverman, L.E. (Editor); *Diseases of the Thyroid*; Humana Press (1997); p. 157.

Cardinal, D.P., et al.; Peripheral Neuroendocrinology of the Cervical Autonomic Nervous System; *Brazilian J. Med. Biol. Res.* (1994); 27(3):573–599.

Fauci, a.S., et al. (Editors); *Harrison's Principles of Internal Medicine* 14$^{th}$ Edition (1998); McGraw–Hill., only editorial pages supplied.

Garry, M.G. et al; Evaluation of the Efficacy of a Bioerodible Bupivacaine Polymer System on Antinociception and Inflammatory Mediator Release; *Pain*; 82(1);49–55 (1999).

Gonelle–Gispert, C., et al.: SNAP–25A AND–25B Isoforms are Both Expressed in Insulin–Secreting Cells and Can Function in Insulin Secretion; *Biochem. J.* (1999); 339:159–165.

Huffman, L.J., et al.; Muscarinic Modulation of the Vasodilatory Effects of Vasodilatory Effects of Vasoactive Intestinal Peptide at the Rat Thyroid Gland: *Neuroendocrinology* (1991);53:69–74.

Lakomy, M., et al.: Acetylcholine Esterase Positive Nerves in Swine Thyroid; *Z. Mikrosk.–anat. Forsch., Leipzig* 100 (1986) 1, S. 34–38.

Laskawi, R., at al.; Up–to–Date Report of Botulinum Toxin Type A Treatment in Patients with Gustatory Sweating (Frey's Syndrome); *Laryngoscope* 108 (Mar. 1998); 381–384.

Melander, A., et al.: Presence and Influence of Cholinergic Nerves in the Mouse Thyroid; *Endocrinology* (1979); 105(1):7–9.

Mercadante, S., et al.: Celiac Plexus Block: A Reappraisal; *Regional Anesthesia and Pain Medicine*; 23(1):37–48 (Jan –Feb 1998).

Ragona, R.M., et al.: Management of Parotid Sialocele with Botulinum Toxin: *Laryngoscope* 109 (Aug. 1999); 1344–1346.

Schantz, E.J. et al.; Properties and Use of Botulinum Toxin and Other Microbial Neurotoxins in Medicine; *Microbiological Reviews*; Mar. 1992 vol. 56, No. 1; 80–99.

(List continued on next page.)

Primary Examiner—Christopher S. F. Low
Assistant Examiner—Chih-Min Kam
(74) Attorney, Agent, or Firm—Martin A. Voet; Robert J. Baran; Carlos A. Fisher

(57) ABSTRACT

A method for treating hypothyroidism by local administration of a neurotoxin, such as a *botulinum* toxin, to a thyroid, thereby reducing an inhibitory effect upon thyroid hormone secretion. A method for treating hyperthyroidism by local administration of a neurotoxin, such as a *botulinum* toxin, to a sympathetic ganglion which innervates the thyroid, thereby reducing a stimulatory effect upon thyroid hormone secretion. Methods for treating calcium metabolism disorders by local administration of a neurotoxin to modulate calcitonin secretion are also disclosed.

8 Claims, No Drawings

OTHER PUBLICATIONS

Singh, B.R.; Critical Aspects of Bacterial Protein Toxins; *Natural Toxins II*(1996); Plenum Press, New York; pp. 63–84.

Stern, J.E., et al.: Influence of the Autonomic Nervous System on Calcium Homeostasis in the Rat; *Biol Signals* (1994); 3:15–25.

Stevens, P.D., et al.; Managing Chronic Pancreatitis Pain: A Block in Time; *AJG*; 94(4):872–874 (1999).

Unger, J., et al.; Mechanism of Cholinergic Inhibition of Dog Thyroid Secretion In Vitro; *Endocrinology*; 1984; 114:1266–1271.

* cited by examiner

METHOD FOR TREATING HYPERCALCEMIA

CROSS REFERENCE

This application is a divisional of Ser. No. 09/504,538, filed Feb. 15, 2000.

BACKGROUND

The present invention relates to methods for treating thyroid disorders. In particular the present invention relates to methods for treating thyroid disorders by administration of a neurotoxin to a patient.

It has been estimated that at least about two hundred million people worldwide are afflicted with a thyroid disorder and women are affected disproportionaly, as compared to men, by a ratio of about ten to one. In the United States, about ten million persons, including ten percent of all women over age 45, have either overactive or underactive thyroid glands. Bayliss et al., *Thyroid Disease The Facts, preface*, Oxford University Press (1998).

Thyroid Function

The thyroid is an endocrine gland comprised of follicle cells and non-follicular or C cells. The follicle cells are capable of making two hormones, triiodothyronine ($T_3$) which contains three iodine atoms and thyroxine ($T_4$) which contains four. The action of thyroid hormone is concerned principally with the regulation of metabolic rate by, for example, increasing energy production and oxygen consumption by most normal tissues. Synthesis and release of $T_3$ and $T_4$ by thyroid cells in influenced by thyroid stimulating hormone (TSH, also called thyrotrophin) made by the pituitary. The C cells can make calcitonin which appears to influence calcium metabolism. Significantly, calcitonin is a potent hypocalcemic agent. Disorders of the thyroid include autoimmune disorders (such as Graves' disease), thyroiditis (inflammation or infection of the thyroid), and cancer, all of which conditions can result in hypothyroidism (as can occur in Hashimoto's thyroiditis) or hyperthyroidism (thyroidtoxicosis, as can occur in Graves' disease). An enlarged thyroid (goiter) can by euthyroid, or a symptom of either hyperthyroidism (thyroidtoxicosis) or hypothyroidism.

Most cases of hyperthyroidism are believed to be due to the action of thyroid stimulating antibodies upon the thyroid as a whole (Graves' disease, diffuse toxic goiter).

Graves' disease has been estimated to occur in 0.4% of the population of the United States, with a lifetime risk of 1%. It is most commonly manifest in the third or fourth decade of life and the female to male ratio is about 7:1 to about 10:1. The thyroid abnormalities characteristic of Graves' disease apparently result from the action of immunoglobulin of the IgG class on the thyroid. These antibodies may be directed against components or regions of the plasma membrane that include the receptor for thyroid simulating hormone (TSH) itself. The principal destabilizing factor resulting in autoimmune thyroid disease appears to be an organ specific defect in suppressor T-lymphocytes. Hyperthyroidism itself appears to have an adverse effect on generalized suppressor T-cell function, and this may be a self-perpetuated or potentiating factor in Graves' disease. Significantly, there is no known cure for Grave's disease, treatment being designed merely to reduce the thyroid's ability to produce thyroid hormones.

Causes of hyperthyroidism besides Graves' disease, include toxic multinodular goiter, toxic adenoma, subacute viral thyroiditis, postpartum thyroiditis, thyroid, gonadal and pituitary tumors and excess pituitary TSH.

The normal thyroid gland weighs about fifteen grams. It is convex anteriorly and concave posteriorly as a result of its relation to the anterolateral portions of the trachea and larynx, to which it is firmly fixed by fibrous tissue. The two lateral lobes of the thyroid extend along the sides of the larynx, reaching the level of the middle of the thyroid cartilage. Each thyroid lobe resides in a bed between the trachea and larynx medially and the carotid sheath and sternocleidomastoid muscles laterally.

The thyroid is composed of an aggregation of spherical or ovate cystlike follicles of variable size. The interfollicular areas are occupied by a highly vascularized network which includes parafollicular cells (C cells) which are responsible for the secretion of calcitonin. Parathyroid hormone (PTH, made by the parathyroid glands), calcitonin (made by the C cells of the thyroid) and dihydroxycholecalciferol (metabolized from vitamin D in the kidney) are the principal hormones concerned with the metabolism of ions such as calcium, phosphate, pyrophosphate, citrate and magnesium, and with the regulation of the metabolism of bone and its organic constituents. In humans, it is believed that calcitonin acts, in a manner antagonistic to PTH, to lower plasma calcium.

The thyroid gland is enveloped by a thickened fibrous capsule. The deep cervical fascia divides into an anterior and a posterior sheath, creating a loosely applied false capsule for the thyroid. Anterior to the thyroid lobes are the strap muscles. Situated on the posterior surface of the lateral lobes of the thyroid gland are the parathyroid glands and the recurrent laryngeal nerves; the latter usually lie in a cleft between the trachea and the esophagus. The lateral lobes of the thyroid are joined by the isthmus that crosses the trachea. A pyramidal lobe is often present. The pyramidal lobe is a long, narrow projection of thyroid tissue extending upward from the isthmus lying on the surface of the thyroid cartilage. It represents a vestige of the embryonic thyroglossal duct.

Thyroid Vascular Supply

The thyroid has an abundant blood supply. Its four major arteries are the paired superior thyroid arteries, which arise from the external carotid arteries and descend several centimeters in the neck to reach the upper poles of each thyroid lobe, where they branch, and the paired inferior thyroid arteries, each of which arises from the thyrocervical trunk of the subclavian artery, runs medially behind the carotid artery and enters the lower or midpart of the thyroid lobe from behind. A fifth artery, the thyroidea ima, is sometimes present; it arises from the arch of the aorta and enters the thyroid in the midline.

A venous plexus forms under the thyroid capsule. Each lobe is drained by the superior thyroid vein at the upper pole and the middle thyroid vein at the middle part of the lobe, both of which enter the internal jugular vein. Arising from each lower pole are the inferior thyroid veins, which drain directly into the innominate vein.

Thyroid Innervation

Significantly, the thyroid gland receives innervation from both the sympathetic and parasympathetic divisions of the autonomic nervous system. The sympathetic fibers arise from the cervical ganglia and enter with blood vessels, whereas the parasympathetic fibers are derived from the vagus and reach the gland via branches of the laryngeal nerves. The thyroid gland's relation to the recurrent laryngeal nerves and to the external branch of the superior laryngeal nerves is of major surgical significance, since damage to these nerves can lead to a disability of phonation.

Sympathetic innervation of the thyroid cells has been reported to exert a stimulatory effect upon thyroid hormone release through adrenergic receptors for norepinephrine on follicle cells. *Endocrinology* 1979;105:7–9. Significantly, the human thyroid is also innervated by cholinergic, parasympathetic fibers. *Cell Tiss Res* 1978;195:367–370. See also *Biol Signals* 1994;3:15–25. And other mammalian species are known to also have cholinergicly innervated thyroid cells. See e.g. *Z. Mikrosk Anat Forsch Leipzig* 1986;100:1,S, 34–38 (pig thyroid is cholinergicly innervated); *Neuroendocrinology* 1991;53:69–74 (rat thyroid is cholinergicly innervated); *Endocrinology* 1984;114:1266–1271 (dog thyroid is cholinergicly innervated);

It has been reported that stimulation of the vagal nerve increases both thyroid blood flow and thyroid hormone secretion (*Cell Tiss Res* 1978;195:367–370), but this is apparently due to the extensive, generalized effect of vagal stimulation which can trigger a number of reflexes ascribed to the whole vagus territory. It is therefore inappropriate to conclude from this observation the vagal stimulation acts directly upon the thyroid to increase thyroid hormone release.

Significantly, the consensus is that cholinergic, parasympathetic influence upon thyroid hormone secretion by thyroid follicle cells, and presumably also of the intimately associated C cells, in inhibitory. *Endocrinology* 1979;105:7–9; *Endocrinology* 1984;114:1266–1271; *Peptides* 1985;6:585–589; *Peptides* 1987;8:893–897, and; *Brazilian J Med Biol Res* 1994;27:573–599. The direct cholinergic influence upon the thyroid appears to be mediated by muscarinic acetylcholine receptors of thyroid follicle cells since the cholinergic inhibition is blocked by atropine. *Endocrinology* 1979;105:7. The proximity of the non-follicular, calcitonin secreting cells of the thyroid to the thyroid hormone secreting follicle cells has led to the conclusion that parasympathetic influence over the C cells is also inhibitory.

Current Therapy

Therapy for thyroid disorders includes systemically administered drugs, radiotherapy and surgical resection. Unfortunately, all three of these current therapeutic procedures to treat thyroid disorders, including Graves' disease, have significant drawbacks and deficiencies.

Drug therapy for hyperthyroidism includes use of the antithyroid drugs propylthiouracil (PTU) and methimazole (Tapazole), both of which inhibit the organic binding of iodide. In addition, propylthiouracil inhibits the peripheral conversion of $T_4$ to $T_3$. Notably, the half-life of propylthiouracil is only about 1.5 hours while that of methimazole is only about 6 hours. The initial dose of propylthiouracil is 200 to 300 mg, up to 1200 mg daily, every 8 to 12 hours or every 4 to 6 hours when large doses are required. The usual regimen of methimazole is 20 to 40 mg daily in one to three divided doses. Such drug therapy is usually prescribed for 12 to 18 months.

As is well known, intravenous, oral or other systemic routes for drug administration can cause many undesirable side effects, including nausea, diarrhea and drug resistance. Additionally, the patient must remember to take the medication. While the antithyroid drugs for treating hyperthyroidism, such as carbimazole, methimazole and propylthiouracil, suppress the ability of the thyroid to make hormones and can render the patient euthyroid, they can also can cause nausea, indigestion, skin rashes, joint pain, fever, and lymphatic gland swelling. Additional side effects include neutropenia and agranulocytosis. Beta adrenergic blocking drugs, such as propranolol (taken orally several times a day), have been used to treat secondary symptoms of hyperthyroidism, such as excessive sweating, tachycardia, hand tremors and anxiety. Iodine has also been used to treat hyperthyroidism due to its a suppressive effect upon the release of thyroid hormones. Unfortunately, this effect lasts for only about 3 or 4 weeks.

Radioactive iodine therapy using $^{131}I$ therapy is designed to administer a sufficient radiation dose to partially destroy the thyroid parenchyma. Biologic effects of $^{131}I$ include pyknosis and necrosis of the follicular cells and, later, vascular and stromal fibrosis. The $^{131}I$ dose, in microcuries ($\mu Ci$), to deliver is calculated using the formula: weight of thyroid gland (gm)×dose ($\mu Ci$/gm)/uptake (%). The weight of the thyroid gland is estimated by palpation and the 24 hour iodine uptake is measured using a tracer dose of $^{123}I$. The dose of $^{131}I$ that is used for treatment of Graves' disease ranges from 70 to 215 $\mu Ci$/gm. Higher doses are associated with less relapse but can also be associated with a higher incidence of hypothyroidism during the first few years following treatment.

Radiation therapy, such as by use of radioactive iodine ($^{131}I$) which concentrates in the thyroid, can by irradiation destroy healthy tissue and cause toxicity reactions, and radiation therapy can have potentially harmful effects. Notably, iodine therapy is not used beyond the first trimester of pregnancy or in children under 15. Additionally, it can take 2 or 3 months before an effect of radio-iodine treatment becomes apparent. Furthermore, the destruction of thyroid cells by radiation therapy can result in hypothyroidism.

Significantly, about 80 percent of Graves' disease patients treated with $^{131}I$ subsequently become hypothyroid. Additionally, there is evidence that the treatment of thyroid overactivity in Graves' disease with radio-iodine may aggravate the various ophthalmopathic conditions more than does treatment with an antithyroid drug. Bayliss et al., supra pages 69–70.

The usual surgical treatment of Graves disease consists of sub-total thyroidectomy leaving 3 to 5 grams of residual thyroid tissue attached to an intact inferior thyroid artery. The choice of therapy may be influenced by cost, age, the size of the goiter, the degree of thyrotoxicosis, pregnancy status, patient preferences, and response to initial treatment. Surgery, because of the potential complications and the cosmetic effect has only a minimal role in the treatment of Graves' disease and is recommended only in patients for whom other therapies are contraindicated or refused.

The surgical option, that is thyroidectomy, has been performed as therapy for thyrotoxicosis, to remove benign and malignant tumors, to alleviate pressure symptoms or respiratory obstruction attributable to the thyroid, and occasionally, to remove an unsightly goiter. Video assisted thyroidectomy has been used to minimize the length of incisions in the neck or to hide the incisions by placing them below the clavicle or far lateral in the neck. The recurrent laryngeal nerve and parathyroid glands can be seen as the thyroid lobectomy is performed. While surgical removal of disfunctional thyroid tissue can be an effective therapy, it is irreversible and depends to a large extent upon the skill of the surgeon. Additionally, some thyroids tumors and cancers are inoperable due to proximity or attachment to vital structures. Furthermore, although the mortality rate accompanying thyroidectomy is very low (reported as 0.19 percent), the morbidity rate is about 13 percent when all complications, including the most minor types are considered.

Complications ensuing from surgery have included hypothyroidism, thyroid storm, wound infection, wound hemorrhage with hematoma formation, recurrent laryngeal nerve injury, hypoparathyroidism and tracheomalacia. Significantly, following total or near-total thyroidectomy patients must take thyroid hormone replacement for the remainder of their lives or suffer severe symptoms and signs of myxedema including tiredness, weakness, depression, psychosis, mental retardation, coma and death.

Notably, about 20% of hyperthyroid patients who have had a surgical thyroidectomy become hypothyroid within one year. Additionally, damage to the recurrent laryngeal nerves during surgery can cause permanent hoarseness of the voice. Furthermore, intraoperative damage to the parathyroids can cause blood calcium levels to fall with resulting tetany.

Thyroid underactivity can be due to a dietary lack of iodine, the lack of which prevents thyroid cell synthesis of the thyroid hormones. In the Western world, Hashimoto's disease is the most common cause of hypothyroidism. Hypothyroidism can also result from radio-iodine treatment or surgery to correct thyroid overactivity, as well as to a pituitary disorder. The treatment of choice for hypothyroidism is replacement therapy with thyroxine. Treatment of hypothyroidism by thyroid hormone replacement requires long term, daily dosing with expensive medication from which undesirable side effects can occur.

Ophthalmopathy

Hyperthyroidism can result in an overactivity of the sympathetic nervous system with resulting eyelid retraction. Other ophthalmic disorders can be the result of autoimmune hyperthyroidism (i.e. Graves' disease and Hashimoto's thyroiditis) when the autoantibodies also affect ocular muscles. Thus, proptosis or exophthalmos (eyes pushed forwards), impaired eye fluid drainage which can cause increased fluid pressure and blindness, ophthalmoplegia (impaired eye muscle control), diplopia (double vision), and blindness. Therapeutic approaches have included beta blockers to reduce lid retraction, surgery to lower the eyelids and to correct the diplopia, corticosteroids (such as prednisone and methylprednisolone) to reduce eye protrusion by suppressing the ocular autoimmune reaction, and X-raying the orbits and surgery to increase the size of the orbits.

Significantly, and as indicated, treatment of hyperthyroidism with $^{131}$I can exacerbate ophthalmopathy more than does treatment with an antithyroid drug. Hence, an effective drug treatment can be preferred to use of radio-iodine or surgery with all its potential complications and required skill level.

Thus, each of the drug, radioactive iodine and surgical therapies for treating thyroid disorders has significant attendant risks, complications, drawbacks and deficiencies. Presently available drugs have only an antithyroid, as opposed to a prothyroid effect, and are administered systemically. Clearly, there is a considerable need for an effective antithyroid drug to treat hyperthyroidism and for a suitable alternative to thyroid hormone replacement to treat hypothyroidism.

Botulinum Toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1996) (where the stated $LD_{50}$ of *botulinum* toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials. One unit of BOTOX® contains about 50 picograms of *botulinum* toxin type A complex.

Seven immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin typeB. Additionally, *botulinum* toxin type B has been determined to be non-toxic in primates at a dose of 480 U/kg which is about 12 times the primate $LD_{50}$ for *botulinum* toxin type A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. *Botulinum* toxin type A has been approved by the U.S. Food and Drug Administration for the treatment of blepharospasm, strabismus and hemifacial spasm. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various *botulinum* toxin serotypes. Significantly, it is known that the cytosol of pancreatic islet B cells contains at least SNAP-25 (*Biochem J* 1;339 (pt 1): 159–65 (April 1999)), and synaptobrevin (*Mov Disord* 1995 May; 10(3): 376).

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. Botulinum toxin types B and $C_1$ is apparently produced as only a 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and non-proteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geq 3\times10^7$ U/mg, an $A_{260}/A_{278}$ of less than 0.60 and a distinct pattern of banding on gel electrophoresis. The known Schantz process can be used to obtain crystalline *botulinum* toxin type A, as set forth in Schantz, E. J., et al, *Properties and use of Botulinum toxin and Other Microbial Neurotoxins in Medicine*, Microbiol Rev. 56: 80–99 (1992). Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of $1–2\times10^8$ $LD_{50}$ U/mg or greater; purified *botulinum* toxin type B with an approximately 156 kD molecular weight with a specific potency of $1–2\times10^8$ $LD_{50}$ U/mg or greater, and; purified *botulinum* toxin type F with an approximately 155 kD molecular weight with a specific potency of $1–2\times10^7$ $LD_{50}$ U/mg or greater.

Already prepared and purified *botulinum* toxins and toxin complexes can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

Pure *botulinum* toxin is so labile that it is generally not used to prepare a pharmaceutical composition. Furthermore, the *botulinum* toxin complexes, such the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be formulated with a stabilizing agent, such as albumin.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N–Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

BOTOX® can be reconstituted with 0.9% Sodium Chloride Injection. Since BOTOX® can be denatured by bubbling or similar violent agitation, the diluent is gently injected into the vial. BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below–5° C. BOTOX® is administered within four hours after the vial is removed from the freezer and reconstituted. During these four hours, reconstituted BOTOX® can be stored in a refrigerator (2° to 8° C.). Reconstituted BOTOX® is clear, colorless and free of particulate matter.

It has been reported that *botulinum* toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

The success of *botulinum* toxin type A to treat a variety of clinical conditions has led to interest in other *botulinum* toxin serotypes. A study of two commercially available *botulinum* type A preparations (BOTOX® and Dysport®) and preparations of *botulinum* toxins type B and F (both obtained from Wako Chemicals, Japan) has been carried out to determine local muscle weakening efficacy, safety and antigenic potential. *Botulinum* toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or *botulinum* toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for *botulinum* toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, *botulinum* toxin type B: 27.0 to 244.0, *botulinum* toxin type F: 4.3. BOTOX® had a longer duration of action than *botulinum* toxin type B or *botulinum* toxin type F. Therapeutic index values were as follows: BOTOX®: 10.5, Dysport®: 6.3, *botulinum* toxin type B: 3.2. Water consumption was greater in mice injected with *botulinum* toxin type B than with BOTOX®, although *botulinum* toxin type B was less effective at weakening muscles. After four months of injections 2 of 4 (where treated with 1.5 ng/kg) and 4 of 4 (where treated with 6.5 ng/kg) rabbits developed antibodies against *botulinum* toxin type B. In a separate study, 0 of 9 BOTOX® treated rabbits demonstrated antibodies against *botulinum* toxin type A. DAS results indicate relative peak potencies of *botulinum* toxin type A being equal to *botulinum* toxin type F, and *botulinum* toxin type F being greater than *botulinum* toxin type B. With regard to duration of effect, *botulinum* toxin type A was greater than *botulinum* toxin type B, and *botulinum* toxin type B duration of effect was greater than *botulinum* toxin type F. As shown by the therapeutic index values, the two commercial preparations of *botulinum* toxin type A (BOTOX® and Dysport®) are different. The increased water consumption behavior observed following hind limb injection of *botulinum* toxin type B indicates that clinically significant amounts of this serotype entered the murine systemic circulation. The results also indicate that in order to achieve efficacy comparable to *botulinum* toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of *botulinum* toxin type B. *Eur J Neurol* 1999 Nov;6(Suppl 4):S3-S10.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and thyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

What is needed therefore is an effective, long lasting, non-surgical resection, non-radiotherapy, non-systemic drug administration, therapeutic drug and method for treating thyroid disorders.

SUMMARY

The present invention meets this need and provides an effective, non-surgical resection, relatively long term, non-radiotherapy, non-systemic drug administration, therapeutic method for treating thyroid disorders. The drug within the scope of this invention for treating thyroid disorders is a neurotoxin. Significantly, the same neurotoxin can be used to treat hypothyroidism, hyperthyroidism, hypocalcemia and hypercalcemia depending upon factors such as the site of local administration of the neurotoxin and the amount of neurotoxin to be administered.

As used herein "local administration" means direct injection of a neurotoxin into the thyroid or into a sympathetic ganglion which innervates a thyroid cell (such as a thyroid follicle cell or thyroid C cell). Systemic routes of administration, such as oral and intravenous routes of administration, are excluded from the scope of "local administration" of a neurotoxin.

As used herein, "thyroid hormone" means thyroxine ($T_4$), while "thyroid hormones" means triiodothyronine ($T_3$) and thyroxine ($T_4$).

A method for treating a thyroid disorder according to the present invention can be carried out by administration of a therapeutically effective amount of a neurotoxin to a patient, thereby treating the thyroid disorder. The neurotoxin can administered to the thyroid of the patient when the thyroid disorder to be treated is hypothyroidism. Alternately, the neurotoxin can be administered to a sympathetic ganglion which innervates the thyroid when the thyroid disorder to be treated is hyperthyroidism.

A detailed method for treating a thyroid disorder according to the present invention can comprise the step of administration of a therapeutically effective amount of a *botulinum* toxin to a patient. Thus, a method for treating hypothyroidism according to the present invention can comprise the step of local administration to the thyroid of a therapeutically effective amount of a *botulinum* toxin, thereby increasing a deficient thyroid hormone secretion from the thyroid cell and effectively treating the hypothyroidism. Furthermore, a method within the scope of the present invention for treating hyperthyroidism, can comprise the step of local administration to a sympathetic ganglion which innervates a thyroid cell of a therapeutically effective amount of a *botulinum* toxin, thereby reducing an excessive thyroid hormone secretion from the thyroid cell and hence effectively treating the hyperthyroidism.

The neurotoxin can be administered in an amount of between about $10^{-3}$ U/kg and about 35 U/kg. 35 U/kg is an upper limit because it approaches a lethal dose of certain neurotoxins, such as *botulinum* toxin type A. Other *botulinum* toxins, such as *botulinum* toxin type B, can be safely administered at several orders of magnitude higher dosage. Preferably, the neurotoxin is administered in an amount of between about $10^{-2}$ U/kg and about 25 U/kg. More preferably, the neurotoxin is administered in an amount of between about $10^{-1}$ U/kg and about 15 U/kg. Most preferably, the neurotoxin is administered in an amount of between about 1 U/kg and about 10 U/kg. In many instances, an administration of from about 1 units to about 500 units of a neurotoxin, such as a *botulinum* toxin type A, provides effective and long lasting therapeutic relief. More preferably, from about 5 units to about 300 units of a neurotoxin, such as a *botulinum* toxin type A, can be used and most preferably, from about 10 units to about 200 units of a neurotoxin, such as a *botulinum* toxin type A, can be locally administered into a target tissue such as the thyroid or a sympathetic ganglion with efficacious results. In a particularly preferred embodiment of the present invention from about 10 units to about 100 units of a *botulinum* toxin, such as. *botulinum* toxin type A, can be locally administered into a target tissue such as the thyroid or a sympathetic ganglion with therapeutically effective results.

The neurotoxin can be made by a Clostridial bacterium, such as by a *Clostridium botulinum, Clostridium butyricum, Clostridium beratti* or *Clostridium tetani* bacterium. Additionally, the neurotoxin can be a modified neurotoxin, that is a neurotoxin that has at least one of its amino acids deleted, modified or replaced, as compared to the native or wild type neurotoxin. Furthermore, the neurotoxin can be a recombinant produced neurotoxin or a derivative or fragment thereof.

The neurotoxin can be a *botulinum* toxin, such as one of the *botulinum* toxin serotypes A, B, $C_1$, D, E, F or G. Preferably, the neurotoxin is *botulinum* toxin type A and the neurotoxin is locally administered by direct injection of the neurotoxin into the thyroid or into a sympathetic ganglion which innervates the thyroid.

A detailed embodiment of a method within the scope of the present invention for treating a thyroid disorder can comprise the step of injecting a therapeutically effective amount of a *botulinum* toxin into a thyroid of a human patient, thereby increasing a thyroid hormone secretion from a thyroid cell and treating a thyroid disorder.

Another detailed embodiment of a method within the scope of the present invention for treating a thyroid disorder of a human patient can comprise the step of local administration to a cholinergic influenced thyroid cell of a human patient of a therapeutically effective amount of *botulinum* toxin type A, thereby increasing a cholinergic influenced deficient thyroid hormone secretion from the thyroid cell and treating the thyroid disorder.

Another method within the scope of the present invention is a method for treating a thyroid disorder by administration of a neurotoxin to a sympathetic nervous system of a patient. In this method the neurotoxin is locally administered to a sympathetic ganglion which innervates a thyroid cell and the thyroid disorder is hyperthyroidism.

A detailed embodiment of a method within the scope of the present invention for treating a thyroid disorder of a human patient can comprise the step of in vivo, local administration to a sympathetic ganglion, which innervates a thyroid cell of a patient, of a therapeutically effective amount of a *botulinum* toxin, thereby decreasing an excessive thyroid hormone secretion from a thyroid cell and treating hyperthyroidism.

A detailed embodiment of the present invention is a method for treating a thyroid disorder by injecting a therapeutically effective amount of a *botulinum* toxin into a thyroid of a human patient, thereby increasing a secretion of a thyroid hormone from a thyroid cell and treating the thyroid disorder. Preferably, the secretion treated is a cholinergic influenced secretion and the *botulinum* toxin used is *botulinum* toxin type A, although the *botulinum* toxin can selected from the group consisting of *botulinum* toxin types A, B, C (i.e. $C_1$), D, E, F and G.

My invention also includes within its scope, a method for treating hypercalcemia, the method comprising the step of local administration to a thyroid C cell of a therapeutically effective amount of a *botulinum* toxin, thereby increasing a deficient calcitonin secretion from a thyroid C cell and treating hypercalcemia. Additionally, my invention also includes within its scope a method for treating hypocalcemia, the method comprising the step of local administration to a sympathetic ganglion which innervates a thyroid C cell of a therapeutically effective amount of a *botulinum* toxin, thereby increasing a deficient calcitonin secretion from the thyroid C cell and treating hypocalcemia.

DESCRIPTION

The present invention is based upon the discovery that a thyroid disorder can be treated by in vivo administration of a neurotoxin to a patient. Thus administration of a neurotoxin to the thyroid of a patient can remove an inhibitory cholinergic effect upon thyroid hormone secretion, thereby providing an effective treatment for hypothyroidism. Additionally, administration of a neurotoxin to a sympathetic ganglion which innervates the thyroid can remove a stimulatory adrenergic effect upon thyroid hormone secretion, thereby providing an effective treatment for hyperthyroidism.

Thus, thyroid disorders can be treated, according to the present invention, by the alternative therapies of (a) local administration of a neurotoxin to the thyroid, or; (b) local administration of a neurotoxin to a sympathetic ganglion of a patient, thereby resulting in, respectively, an increase of a secretion from a thyroid cell, or a decrease in a secretion from a thyroid cell.

I have discovered that a particular neurotoxin, *botulinum* toxin, can be used with dramatic ameliorative effect to treat a thyroid disorder, thereby significantly superseding thereby current therapeutic regimens, such as oral thyroid hormone (to treat hypothyroidism) or radioactive iodine (to treat hyperthyroidism). Significantly, a single local administration of a neurotoxin, such as a *botulinum* toxin to the thyroid, according to the present invention, can increase thyroid hormone secretion and thereby treat symptoms of hypothyroidism. I have also discovered that a single local administration of a neurotoxin, such as a *botulinum* toxin to a sympathetic ganglion which innervates the thyroid gland, according to the present invention, can reduce thyroid hormone secretion and thereby treat symptoms of hyperthyroidism. In either case, the symptoms of the thyroid disorder can be alleviated for at least about from 2 months to about 6 months per neurotoxin administration. Notably, it has been reported that glandular tissue treated by a *botulinum* toxin can show a reduced secretory activity for as long as 27 months post injection of the toxin. *Laryngoscope* 1999; 109:1344–1346, *Laryngoscope* 1998; 108:381–384.

The hypothyroidism treatable by the present invention is hypothyroidism which has as a causative factor the inhibitory activity upon thyroid hormone secretion of parasympathetic innervation of the thyroid. Thus, treatment of hypothyroidism which results directly and solely from, for example, a dietary iodine deficiency or from the action of anti-thyroid antibodies, is outside the scope of the present invention. Similarly, the hyperthyroidism treatable by the present invention is hyperthyroidism which has as a causative factor the stimulatory activity upon thyroid hormone secretion of sympathetic innervation of the thyroid. Thus, treatment of hyperthyroidism which results directly and solely from, for example, the effect of thyroid stimulating antibodies upon the thyroid is outside the scope of the present invention.

Notably, hypothyroidism resulting from a combination of factors, including inhibitory parasympathetic activity, is treatable by a method within the scope of the present invention. Similarly, hyperthyroidism resulting from a combination of factors, including stimulatory sympathetic activity, is treatable by a method within the scope of the present invention.

Local Administration of a Neurotoxin to the Thyroid

A preferred embodiment of the present invention is to inject the thyroid of a patient with from 1 to 500 units, more preferably from 10 to 200 units, and most preferably from 20 to 100 units of a neurotoxin (such as a *botulinum* toxin type A), to thereby cause a reduction of thyroid follicle hormone secretion. The present invention also includes within its scope treatment of a thyroid disorder due to hyperplasic, hypertonic or hypertrophic thyroid follicle cells. A thyroid disorder can be effectively treated by local administration of a neurotoxin, such as for example 10 to 500 units of *botulinum* toxin type A, to cholinergic, postganglionic, parasympathetic neurons which innervate the dysfunctional, thyroid cells. Without wishing to be bound by theory, the *botulinum* toxin is believed to act by inhibiting release of acetylcholine neurotransmitter from cholinergic, postganglionic parasympathetic fibers which innervate thyroid follicle cells.

A neurotoxin, such as a *botulinum* toxin, can be locally administered in vivo to the thyroid to thereby remove an inhibitory effect upon a secretory activity of a thyroid follicle cell. The thyroid follicle cell is cholinergically innervated or susceptible to high toxin dosing such that the proteolytic light chain of the toxin is internalized by a cholinergic neuron which influences a secretory activity of the thyroid cell.

Thus, cholinergically innervated thyroid cells can be treated by local administration of a neurotoxin, such as a *botulinum* toxin. By local administration it is meant that the neurotoxin is administered directly to or to the immediate vicinity of the thyroid tissue to be treated.

The specific dosage appropriate for administration is readily determined by one of ordinary skill in the art according to the factor discussed above. The dosage can also depend upon the size of the thyroid tissue mass to be treated or denervated, and the commercial preparation of the toxin. Additionally, the estimates for appropriate dosages in humans can be extrapolated from determinations of the amounts of *botulinum* required for effective denervation of other tissues. Thus, the amount of *botulinum* A to be injected is proportional to the mass and level of activity of the thyroid tissue to be treated. Generally, between about 0.01 and 35 units per kg of patient weight of a *botulinum* toxin, such as *botulinum* toxin type A, can be administered to effectively accomplish a toxin induced thyroid tissue secretion up regulation upon administration of the neurotoxin into the thyroid. Less than about 0.01 U/kg of a *botulinum* toxin does not have a significant therapeutic effect upon the secretory activity of a thyroid cell, while more than about 35 U/kg of a *botulinum* toxin approaches a toxic dose the neurotoxin. Careful placement of the injection needle and a low volume of neurotoxin used prevents significant amounts of *botulinum* toxin from appearing systemically. A more preferred dose range is from about 0.01 U/kg to about 25 U/kg of a *botulinum* toxin, such as that formulated as BOTOX®. The actual amount of U/kg of a *botulinum* toxin to be administered depends upon factors such as the extent (mass) and level of activity of the thyroid tissue to be treated and the administration route chosen. *Botulinum* toxin type A is a preferred *botulinum* toxin serotype for use in the methods of the present invention.

It has been reported that the neuronal selectivity of clostridial neurotoxins is a result of a very selective binding and cell entry mechanism. Although a site of action of *botulinum* toxin is the neuromuscular junction, where the toxin binds rapidly and prevents the release of acetylcholine from cholinergic neurons, it is known that clostridial neurotoxins are able to enter certain neurosecretory cells (for example PC12 cells) via a low affinity receptor if high concentrations of the neurotoxin are incubated with the cells for prolonged periods. This process appears to use a pathway via a receptor which is distinct from the highly specific and high affinity receptor present at the neuromuscular junction. Additionally, it has been reported that certain clostridial toxins have effects on phagocyte cells, such as macrophages, where entry into the cell is presumed to be via the specific phagocytic activity of these cells. Furthermore, incubation of certain adipocytes (i.e. fat cells) with *botulinum* toxin type A has been reported to inhibit glucose uptake by the adipocytes. The mechanism of the glucose uptake inhibition is apparently due to toxin inhibition of plasma membrane fusion or docking of cytosolic, recyclable membrane vesicles (RMVs), the RMVs containing glucose transporter proteins. PCT publication WO 94/121300.

Thus, while it is known that the *botulinum* toxins have a known binding affinity for cholinergic, pre-synaptic, peripheral motor neurons, it has been reported that *botulinum* toxins can also bind to and translocate into a variety of non-neuronal secretory cells, where the toxin then acts, in the known manner, as an endoprotease upon its respective secretory vessel-membrane docking protein. Because of the relatively lower affinity of the *botulinum* toxins for secretory cells, such as thyroid cells, as compared to the affinity of the *botulinum* toxin for the cholinergic neurons which innervate thyroid cells, the *botulinum* toxin can be injected into secretory or glandular tissues to provide a high local concentration of the toxin, thereby facilitating effect of the toxin upon both cholinergic neuron and directly upon thyroid secretory cell. Thus, the present invention is applicable to the treatment of thyroid disorders wherein the target thyroid cells have little or no cholinergic innervation.

Preferably, a neurotoxin used to practice a method within the scope of the present invention is a *botulinum* toxin, such as one of the serotype A, B, C, D, E, F or G *botulinum* toxins. Preferably, the *botulinum* toxin used is *botulinum* toxin type A, because of its high potency in humans, ready availability, and known safe and efficacious use for the treatment of skeletal muscle and smooth muscle disorders when locally administered by intramuscular injection.

The present invention includes within its scope the use of any neurotoxin which has a long duration therapeutic effect when locally applied to treat a thyroid cell disorder of a patient. For example, neurotoxins made by any of the species of the toxin producing Clostridium bacteria, such as *Clostridium botulinum, Clostridium butyricum*, and *Clostridium beratti* can be used or adapted for use in the methods of the present invention. Additionally, all of the *botulinum* serotypes A, B, C, D, E, F and G can be advantageously used in the practice of the present invention, although type A is the most preferred serotype, as explained above. Practice of the present invention can provide effective relief of a thyroid disorder for from 2–27 months or longer in humans.

*Botulinum* toxin is believed to be able to block the release of any vesicle mediated exocytosis from any secretory (i.e. neuronal, glandular, secretory, chromaffin) cell type, as long as the light chain of the *botulinum* toxin is translocated into the intracellular medium. For example, the intracellular protein SNAP-25 is widely distributed in both neuronal and non-neuronal secretory cells and *botulinum* toxin type A is an endopeptidase for which the specific substrate is SNAP-25. Thus, while cholinergic neurons have a high affinity acceptor for the *botulinum* and tetanus toxins (and are therefore more sensitive than other neurons and other cells to the inhibition of vesicle mediated exocytosis of secretory compounds), as the toxin concentration is raised, non-cholinergic sympathetic neurons, chromaffin cells and other cell types can take up a *botulinum* toxin and show reduced exocytosis.

Hence, by practice of the present disclosed invention, non-cholinergic nerve fibers as well as non or poorly innervated thyroid cells can be treated by use of an appropriately higher concentration of a *botulinum* toxin to bring about therapeutic relief from a thyroid disorder.

Local Administration of a Neurotoxin to a Sympathetic Ganalion

Significantly, a method within the scope of the present invention for reducing an excessive thyroid hormone secretion comprises the step of local administration of a neurotoxin to the sympathetic nervous system. Sympathetic innervation of the thyroid is know to exist. Thus, sympathetic nerve fibers can stimulate thyroid hormone secretion by acting via adrenergic receptors on thyroid follicles. A method within the scope of the present invention can therefore be carried out by local administration of a neurotoxin to a cholinergic, preganglionic sympathetic neuron. The cholinergic, preganglionic, sympathetic neurons synapse with adrenergic, post-ganglionic, sympathetic fibers, and these later sympathetic neurons have a stimulatory effect upon thyroid hormone secretion by thyroid cells. Preferably, the sympathetic ganglion to which a neurotoxin is administered, according to the preset invention, is a cervical ganglion.

Cervical ganglion block according to the present invention can be carried out in the same manner as a celiac plexus block. Thus, the neurolytic celiac plexus block is a known procedure for treating intractable pain resulting from upper abdominal viscera cancer. *Reg Anest Pain Med* 1998; 23(1):37–48. Thus, it is known to inject the celiac plexus with ethanol or phenol to provide relief from the pain which can result from pancreatic cancer or from pancreatitis. *AJG* 1999;94(4):872–874. Hence, an antinociceptive injection of the cervical ganglia can be carried out as by either a percutaneous procedure or as an open (intraoperative) injection. The percutaneous (closed) procedure can be carried out using an anterior approach using a very thin needle (22 Gauge). Cervical ganglion block is preferably carried out with computed tomography (CT) (as opposed to fluoroscopic) needle guidance, using a single thin needle.

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting therapeutic effect can be achieved by local administration of a neurotoxin to the thyroid or to a sympathetic ganglion which innervates the thyroid of a human patient. In its most preferred embodiment, the present invention is practiced by direct injection into the thyroid or into the sympathetic ganglion of *botulinum* toxin type A. It has been reported that at the neuroglandular junction, the chemical denervation effect of a *botulinum* toxin, such as *botulinum* toxin type A, has a long duration of action, i.e. 27 months vs. 3 months.

The present invention includes within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on a thyroid cell.

*Botulinum* toxins for use according to the present invention can be stored in lyophilized or vacuum dried form in containers under vacuum pressure. Prior to lyophilization the *botulinum* toxin can be combined with pharmaceutically acceptable excipients, stabilizers and/or carriers, such as albumin. The lyophilized or vacuum dried material can be reconstituted with saline or water.

The route of administration and amount of a neurotoxin (such as a *botulinum* toxin serotype A, B, C, D, E, F or G) administered according to the present invention for treating a thyroid disorder can vary widely according to various patient variables including size, weight, age, disease severity, responsiveness to therapy, and solubility and diffusion characteristics of the neurotoxin toxin chosen. Furthermore, the extent of the thyroid or ganglionic tissue influenced is believed to be proportional to the volume of neurotoxin injected, while the quantity of the denervation is, for most dose ranges, believed to be proportional to the concentration of neurotoxin injected.

Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, to treat a thyroid disorder, a solution of *botulinum* toxin type A complex can be endoscopically or intraperitoneally injected directly into the tissues of the thyroid, thereby substantially avoiding entry of the toxin into the systemic circulation.

EXAMPLES

The following examples provide those of ordinary skill in the art with specific preferred methods within the scope of the present invention for carrying out the present invention and are not intended to limit the scope of what the inventor regards as his invention. In each of the following examples, the specific amount of a *botulinum* toxin administered depends upon a variety of factors to be weighed and considered within the discretion of the attending physician and in each of the examples insignificant amounts of *botulinum* toxin enter appear systemically with no significant side effects. Units of *botulinum* toxin injected per kilogram (U/kg) below are per kg of total patient weight. For example, 3 U/kg for a 70 kg patient calls for an injection of 210 units of the *botulinum* toxin.

Example 1

Intraoperative Administration of Neurotoxin

Intraoperative, local administration of a neurotoxin to the thyroid can be carried out as follows. The procedure can be performed under general endotracheal anesthesia. The patient's neck can be extended by inflating a pillow or inserting a thyroid roll beneath the shoulders. A symmetrical, low, collar incision can then be made in the line of a natural skin crease approximately 1 to 2 cm above the clavicle. The incision can be carried through the skin, subcutaneous tissue, and platysma muscle down to the dense cervical fascia that overlies the strap muscles and anterior jugular veins. The upper flap can then be raised to a level cephalad to the cricoid cartilage. Care is taken to avoid cutting sensory nerves. A small lower flap is also elevated to the level of the manubrial notch. Performing dissection of the flaps in the plane between the platysma muscle and the fascia overlying the strap muscles results in minimal bleeding. The cervical fascia is then incised vertically in the midline from the thyroid cartilage to the sternal notch.

Exposure of the superior and lateral aspects of the thyroid gland is achieved by retracting the sternohyoid and sternothyroid muscles laterally or in very large glands by dividing these muscles. Division of these muscles is associated with little or no disability, but is not necessary unless the gland is markedly enlarged. High transection is preferable, since the ansa cervicalis nerve innervates the muscles from below. This procedure diminishes the amount of muscle that is paralyzed.

Digital or blunt dissection frees the thyroid from the surrounding fascia. As an initial step, the isthmus of the thyroid is usually revealed. Rotation of one lobe of the thyroid can be followed by dissection bluntly. The middle thyroid veins are first encountered and are ligated and divided. This maneuver facilitates exposure of the superior and inferior poles of the thyroid lobe. The suspensory ligaments are transected craniad to the isthmus, and the pyramidal lobe and Delphian nodes are mobilized. The cricothyroid space is opened in order to separate the superior pole from the surrounding tissue. If dissection of the superior lobe is to be carried out (i.e. thyroidectomy in conjunction with neurotoxin administration), care is taken to avoid injury to the superior laryngeal nerve. The internal branch of the nerve, which provides sensory fibers to the epiglottis and larynx, is rarely in the operative field. It is the external branch, which supplies motor innervation to the inferior pharyngeal constrictor and the cricothyroid muscle, that must be protected. This purpose is achieved by dissecting the nerve away from the superior pole vessels if it can be identified, or by separately ligating and dividing the individual branches of the superior thyroid vessels immediately adjacent to the upper pole of the thyroid lobe rather than cephalad to it.

The lobe can then be retracted mediad to permit identification of the inferior thyroid artery and the recurrent laryngeal nerve. It is essential that meticulous hemostasis be achieved during this part of the dissection. The inferior thyroid artery is isolated, but need not be ligated laterally. Rather, when performing a lobectomy, it is preferable to ligate and divide each small arterial branch near the thyroid capsule at a point after branches to the parathyroid glands have been given off. This technique lessens the incidence of devascularization of the parathyroid gland and plays a role in reducing permanent hypoparathyroidism. If a parathyroid gland is devascularized it can be minced and autotransplanted into the sternocleidomastoid after being verified by frozen section analysis. The recurrent laryngeal nerve can be identified along its course by blunt dissection. The fibrous tissues are gently unroofed from the front of the nerve. The nerve is treated with care, for excessive trauma or its division will result in an ipsilateral vocal cord paralysis. At the junction of the trachea and larynx, the recurrent laryngeal nerve is immediately adjacent to the thyroid lobe and is in greatest danger, if it is not seen. The exposed thyroid lobe can now be directed injected with from 10 to 300 units of a *botulinum* toxin, such as *botulinum* toxin type A.

During exposure of the posterior surface of the thyroid gland, the parathyroid glands should be identified and preserved, along with their vascular pedicles. Care should be taken to ensure that the parathyroid glands are not excised or devascularized.

The entire wound is then inspected, and careful hemostasis is obtained before closure. In most instances, a suction catheter is used to drain the bed of the thyroid lobes, employing a small, soft plastic drain that is brought out through a stab wound lateral to the incision. The postoperative wound appearance with this technique is far superior to that obtained when no drainage is employed. If the sternothyroid and sternohyoid muscles have been transected, they are reapproximated. The midline vertical fascial incision is only loosely approximated by one interrupted suture, and the drain is positioned superficial to the strap muscles. There is generally no need to suture the platysma muscle, instead it is preferable to approximate the deep dermis with interrupted 4-0 resorbable sutures and the epithelium with 5-0 continuous subcuticular sutures. Finally, the epithelial surfaces are approximated with sterile skin tapes. Within one to seven days, thyroid hormone secretion is substantially increased due to removal of cholinergic inhibition and this effect persists for from 2 to 6 months.

Example 2

Local Administration of Neurotoxin to the Thyroid

Local administration of a neurotoxin directly to or to the vicinity of the thyroid can be accomplished by several methods. For example, by thyroid endoscopy. An endoscope used for thyroid therapy can be modified to permit its use for direct injection of a neurotoxin, such as a *botulinum* toxin directly into thyroid tissue. See for example U.S. Pat. No. 5,674,205. Once appropriately located, a hollow needle tip can be extended from the endoscope into thyroid tissue and through which needle the neurotoxin can be injected into the thyroid tissue. Additionally, fine needle aspiration for thyroid biopsy purposes is well known and can be used to inject a neurotoxin, rather than to aspirate thyroid tissue. From 10 to 300 units of a *botulinum* toxin, such as *botulinum* toxin type A can thereby be injected into the thyroid. Within one to seven days, thyroid hormone secretion is substantially increased due to removal of cholinergic inhibition and this effect persists for from 2 to 6 months.

Example 3

Treatment of Hypothyroidism with *Botulinum* Toxin Type A

A 43 year old, obese man presents with increasing fatigue over the last eight months and worsening pedal and calf edema over same time period, which is exacerbated upon standing for very long. Patient also has had polydipsia and low urine output over same time period. Notably, TSH is 690 (normal is 3–5). A diagnosis of hypothyroidism is made. Between about $10^{-3}$ U/kg and about 35 U/kg of a *botulinum* toxin type A preparation (for example between about 10 units and about 300 units of BOTOX®) is injected directly into the thyroid, using one of the techniques set forth in Examples 1 or 2 above. Within 1–7 days the symptoms of the hypothyroidism are alleviated. Thyroid hormone levels return to substantially normal levels. Alleviation of the hypothyroidism persists for at least about 2 months to about 6 months.

Example 4

Treatment of Hypothyroidism with *Botulinum* Toxin Type B

A 52 year old female is diagnosed with hypothyroidism. Between about $10^{-3}$ U/kg and about 35 U/kg of a *botulinum* toxin type B preparation (for example between about 1000 units and about 20,000 units of a *botulinum* type B preparation) is injected directly into the thyroid, using one of the techniques set forth in Examples 1 or 2 above. Within 1–7 days the symptoms of the hypothyroidism are alleviated. Thyroid hormone levels return to substantially normal levels. Alleviation of the thyroid disorder persists for at least about 2 months to about 6 months.

Example 5

Treatment of Hypothyroidism with *Botulinum* Toxin Type C

A 58 year old female is diagnosed with hypothyroidism. Between about $10^{-3}$ U/kg and about 35 U/lkg of a *botulinum* toxin type C preparation (for example between about 10 units and about 10,000 units of a *botulinum* type C preparation) is injected directly into the thyroid, using one of the techniques set forth in Examples 1 or 2 above. Within 1–7 days the symptoms of the hypothyroidism are alleviated. Thyroid hormone levels return to substantially normal levels. Alleviation of the thyroid disorder persists for at least about 2 months to about 6 months.

Example 6

Treatment of Hypothyroidism with *Botulinum* Toxin Type D

A 56 year old obese female is diagnosed with hypothyroidism. Between about $10^{-3}$ U/kg and about 35 U/kg of a *botulinum* toxin type D preparation (for example between about 10 units and about 10,000 units of a *botulinum* type D preparation) is injected directly into the thyroid, using one of the techniques set forth in Examples 1 or 2 above. Within 1–7 days the symptoms of the hypothyroidism are alleviated. Thyroid hormone levels return to substantially normal levels. Alleviation of the thyroid disorder persists for at least about 2 months to about 6 months.

Example 7

Treatment of Hypothyroidism with *Botulinum* Toxin Type E

A 61 year old female is diagnosed with hypothyroidism. Between about $10^{-3}$ U/kg and about 35 U/kg of a *botulinum* toxin type E preparation (for example between about 10 units and about 10,000 units of a *botulinum* type E preparation) is injected directly into the thyroid, using one of the techniques set forth in Examples 1 or 2 above. Within 1–7 days the symptoms of the hypothyroidism are alleviated. Thyroid hormone levels return to substantially normal levels. Alleviation of the thyroid disorder persists for at least about 2 months to about 6 months.

Example 8

Treatment of Hypothyroidism with *Botulinum* Toxin Type F

A 52 year old male is diagnosed with hypothyroidism. Between about $10^{-3}$ U/kg and about 35 U/kg of a *botulinum* toxin type F preparation (for example between about 10 units and about 10,000 units of a *botulinum* type F preparation) is injected directly into the thyroid, using one of the techniques set forth in Examples 1 or 2 above. Within 1–7 days the symptoms of the hypothyroidism are alleviated. Thyroid hormone levels return to substantially normal levels. Alleviation of the thyroid disorder persists for at least about 2 months to about 6 months.

Example 9

Treatment of Hypothyroidism with *Botulinum* Toxin Type G

A 59 year old female is diagnosed with hypothyroidism. Between about $10^{-3}$ U/kg and about 35 U/kg of a *botulinum* toxin type G preparation (for example between about 10 units and about 10,000 units of a *botulinum* type G preparation) is injected directly into the thyroid, using one of the techniques set forth in Examples 1 or 2 above. Within 1–7 days the symptoms of the hypothyroidism are alleviated. Thyroid hormone levels return to substantially normal levels. Alleviation of the thyroid disorder persists for at least about 2 months to about 6 months.

Example 10

Treatment of Hyperthyroidism with *Botulinum* Toxin Type A

A 27 year old female presents with symptoms and signs of hyperthyroidism, including thyrotoxicosis and bilateral ophthalmopathy. Thyroid function tests confirmed the diagnosis of hyperthyroidism. Thyroid scintigraphy shows an enlarged gland and indicates thyroid hyperplasia. A trial with atropine reduced the thyroid hormone level. Between about $10^{-3}$ U/kg and about 35 U/kg of a *botulinum* toxin type A preparation (for example between about 10 units and about 300 units of BOTOX®) is injected directly into the cervical ganglia as follows. A percutaneous procedure is carried out using an anterior approach with the patient in a supine position using a very thin needle (22 Gauge) with computed tomography needle guidance to reach the cervical ganglia. Within 1–7 days the symptoms of the hyperthyroidism are alleviated. Thyroid hormone levels return to normal (are lowered). Alleviation of the a thyroid disorder persists for at least about 2 months to about 6 months.

Example 11

Treatment of Hyperthyroidism with *Botulinum* Toxin Types B–G

A 62 year old female is diagnosed with hyperthyroidism. Between about $10^{-3}$ U/kg and about 35 U/kg of a *botulinum* toxin type B, C, D, E, F or G preparation (for example between about 10 units and about 20,000 units of a *botulinum* toxin type B, C, D, E, F or G preparation) is injected directly into the cervical ganglia as follows. A percutaneous procedure is carried out using an anterior approach with the patient in a supine position using a very thin needle (22 Gauge) with computed tomography needle guidance to reach the cervical ganglia. Within 1–7 days the symptoms of the hyperthyroidism are alleviated. Thyroid hormone levels return to normal (are lowered). Alleviation of the thyroid disorder persists for at least about 2 to about 6 months.

Example 12

Treatment of Calcium Metabolism Disorders with *Botulinum* Toxin Types A–G

A 28 year old female is diagnosed with hypercalcemia. Between about $10^{-3}$ U/kg and about 35 U/kg of a *botulinum* toxin type A, B, C, D, E, F or G preparation (for example between about 10 units and about 200 units of a *botulinum* toxin type A preparation) is injected directly into the thyroid using one of the techniques set forth in Examples 1 or 2 above. Within 1–7 days the symptoms of the hypercalcemia are alleviated. Plasma calcium levels return to substantially normal levels. Alleviation of the hypercalcemia persists for at least about 2 months to about 6 months.

Additionally, to treat hypocalcemia between about $10^{-3}$ U/kg and about 35 U/kg of a *botulinum* toxin type A, B, C, D, E, F or G preparation (for example between about 10 units and about 200 units of a *botulinum* toxin type A preparation) is injected directly into the cervical ganglia as follows. A percutaneous procedure is carried out using an anterior approach with the patient in a supine position using a very thin needle (22 Gauge) with computed tomography needle guidance to reach the cervical ganglia. Within 1–7 days the symptoms of the hypocalcemia are alleviated. Plasma calcium levels return to normal (are increased). Alleviation of the hypocalcemia persists for at least about 2 to about 6 months.

Methods according to the invention disclosed herein has many advantages, including the following:

(1) the invention renders unnecessary many surgical procedures for effective treatment of a thyroid disorder.

(2) systemic drug effects can be avoided by direct local application of a neurotoxin according to the present invention.

(3) the ameliorative effects of the present invention can persists, on average, from about 2 months to about 6 months from a single local administration of a neurotoxin as set forth herein.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local thyroid administration methods wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type E. Alternately, a combination of any two or more of the *botulinum* serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

My invention also includes within its scope the use of a neurotoxin, such as a *botulinum* toxin, in the preparation of a medicament for the treatment of a thyroid disorder by local administration of the neurotoxin.

Accordingly, the spirit and scope of the following claims should not be limited to the description of the preferred embodiments set forth above.

I claim:

1. A method for treating hypercalcemia, the method comprising the step of local administration to a thyroid of a patient of a therapeutically effective amount of a *botulinum* toxin, thereby-treating hypercalcemia by reducing the patients' plasma calcium level for up to six months.

2. The method of claim 1, wherein the *botulinum* toxin is administered in an amount between $10^{-3}$ U/kg and 35 U/kg.

3. The method of claim 1, wherein the *botulinum* toxin is made by a *Clostridial bacterium*.

4. The method of claim 1, wherein the *botulinum* toxin is selected from the group consisting of *botulinum* toxin types A, B, $C_1$, D, E, F and G.

5. The method of claim 1, wherein the *botulinum* toxin is *botulinum* toxin type A.

6. A method for treating a hypercalcemia, the method comprising the step of local administration to a thyroid of a patient of a therapeutically effective amount of a *botulinum* toxin type A, thereby treating hypercalcemia by reducing the patients' plasma calcium level for up to six months.

7. A method for treating hypercalcemia, the method comprising the step of local administration to a thyroid C cell of a therapeutically effective amount of a *botulinum* toxin, thereby increasing a deficient calcitonin secretion from a thyroid C cell for up to six months and treating hypercalcemia.

8. The method of claim 7, wherein the *botulinum* toxin is selected from the group consisting of *botulinum* toxin types A, B, $C_1$, D, E, F and G.

* * * * *